US011662280B2

(12) United States Patent
Hernandez et al.

(10) Patent No.: US 11,662,280 B2
(45) Date of Patent: May 30, 2023

(54) HI-FIDELITY BIOAEROSOL CONDENSATION CAPTURE DIRECTLY INTO GENOMIC PRESERVATIVES

(71) Applicants: THE REGENTS OF THE UNIVERSITY OF COLORADO, A BODY CORPORATE, Denver, CO (US); AEROSOL DEVICES, INC., Fort Collins, CO (US)

(72) Inventors: Mark Hernandez, Boulder, CO (US); Patricia B. Keady, Fort Collins, CO (US)

(73) Assignees: THE REGENTS OF THE UNIVERSITY OF COLORADO, A BODY CORPORATE, Denver, CO (US); AEROSOL DEVICES, INC., Fort Collins, CO (US)

( * ) Notice: Subject to any disclaimer, the term of this patent is extended or adjusted under 35 U.S.C. 154(b) by 178 days.

(21) Appl. No.: 16/958,421

(22) PCT Filed: Dec. 27, 2018

(86) PCT No.: PCT/US2018/067687
§ 371 (c)(1),
(2) Date: Jun. 26, 2020

(87) PCT Pub. No.: WO2019/133718
PCT Pub. Date: Jul. 4, 2019

(65) Prior Publication Data
US 2021/0055187 A1 Feb. 25, 2021

Related U.S. Application Data

(60) Provisional application No. 62/611,907, filed on Dec. 29, 2017.

(51) Int. Cl.
*G01N 1/22* (2006.01)

(52) U.S. Cl.
CPC ......... *G01N 1/2273* (2013.01); *G01N 1/2214* (2013.01); *G01N 2001/2223* (2013.01); *G01N 2001/2282* (2013.01)

(58) Field of Classification Search
CPC ............... G01N 1/2273; G01N 1/2214; G01N 2001/2223; G01N 2001/2283; G01N 2001/2282; G01N 1/22
(Continued)

(56) References Cited

U.S. PATENT DOCUMENTS

| 3,738,751 A | 6/1973 | Rich | 356/37 |
| 3,806,248 A | 4/1974 | Sinclair | 356/37 |

(Continued)

OTHER PUBLICATIONS

Fierer, N. et al. (2008) "Short-term temporal variability in airborne bacterial and fungal populations," *Applied and Environmental Microbiology* 74(1), 200-207.
(Continued)

*Primary Examiner* — Robert R Raevis
(74) *Attorney, Agent, or Firm* — Medlen & Carroll, LLP (57) ABSTRACT

This invention relates generally to characterizing bioaerosols and, more particularly, to a system for recovering, quantifying, identifying, and assessing the metabolic activities of bioaerosols based on their major biopolymer profiles (lipids, carbohydrate and protein) and more specific their genetic materials (DNA/RNA), such as airborne viruses, bacteria, fungi and pollens.

5 Claims, 3 Drawing Sheets

(58) Field of Classification Search
USPC ............... 436/6.1, 6.11, 30; 73/28.02, 28.04, 73/31.01, 31.02, 31.07, 863, 863.12, 864
See application file for complete search history.

(56) References Cited

U.S. PATENT DOCUMENTS

| | | | |
|---|---|---|---|
| 4,449,816 A | 5/1984 | Kohsaka et al. | 356/37 |
| 4,790,650 A | 12/1988 | Kohsaka et al. | 356/37 |
| 4,868,398 A | 9/1989 | Mulcey et al. | 250/458.1 |
| 4,950,073 A | 8/1990 | Sommer | 356/37 |
| 5,675,405 A | 10/1997 | Schildmeyer et al. | 356/37 |
| 5,855,652 A | 1/1999 | Talley | 356/37 |
| 5,902,385 A | 5/1999 | Willeke et al. | 96/316 |
| 6,506,345 B1 | 1/2003 | Talley | 422/70 |
| 6,567,157 B1 | 5/2003 | Flagan et al. | 356/37 |
| 6,712,881 B2 | 3/2004 | Hering et al. | 95/228 |
| 6,806,464 B2 | 10/2004 | Stowers et al. | 250/282 |
| 6,980,284 B2 | 12/2005 | Ahn et al. | 356/37 |
| 7,736,421 B2 | 6/2010 | Hering et al. | 95/225 |
| 7,777,867 B2 | 8/2010 | Hopke et al. | 356/37 |
| 7,828,273 B2 | 11/2010 | Mölter et al. | 216/128 |
| 8,449,657 B2 | 5/2013 | Son et al. | 95/288 |
| 8,465,791 B2 | 6/2013 | Liu et al. | 427/8 |
| 8,603,247 B2 | 12/2013 | Liu et al. | 118/726 |
| 8,801,838 B2 | 8/2014 | Hering et al. | 95/288 |
| 9,610,531 B2 | 4/2017 | Hering et al. | |
| 2002/0134137 A1 | 9/2002 | Ondov et al. | 73/28.05 |
| 2010/0186524 A1 | 7/2010 | Ariessohn et al. | 73/863.22 |
| 2011/0005932 A1 | 1/2011 | Jovanovich et al. | 436/94 |
| 2014/0060155 A1* | 3/2014 | Hering | G01N 1/2202 73/863.22 |
| 2014/0065602 A1 | 3/2014 | Milton et al. | 435/6.12 |
| 2016/0076073 A1 | 3/2016 | Ensor et al. | 436/178 |

OTHER PUBLICATIONS

Georgakopoulos, D. G. et al. (2009) "Microbiology and atmospheric processes: biological, physical and chemical characterization of aerosol particles," *Biogeosciences* 6(4), 721-737.

Hogan, C. J. et al. (2005) "Sampling methodologies and dosage assessment techniques for submicrometre and ultrafine virus aerosol particles," *Journal of Applied Microbiology* 99(6), 1422-1434.

Iida, K. et al. (2008) "An Ultrafine, Water-Based Condensation Particle Counter and its Evaluation under Field Conditions," *Aerosol Science and Technology* 42(10), 862-871.

Levin, H. et al. (2015) "Summary of Sloan symposium: healthy buildings 2015—Europe," *Microbiome* 3(1), 68.

Mensah-Attipoe, J. et al. (2017) "An emerging paradox: Toward a better understanding of the potential benefits and adversity of microbe exposures in the indoor environment," *Indoor Air* 27(1), 3-5.

Peccia, J. et al. (2006) "Incorporating polymerase chain reaction-based identification, population characterization, and quantification of microorganisms into aerosol science: A review," *Atmospheric Environment* 40(21), 3941-3961.

Walls, H. J. et al. (2016) "Generation and sampling of nanoscale infectious viral aerosols," *Aerosol Science and Technology* 50(8), 802-811.

Xu, Z. et al. (2013) "Enhancing Bioaerosol Sampling by Andersen Impactors Using Mineral-Oil-Spread Agar Plate," *PLoS ONE* 8(2), e56896.

PCT International Search Report of International Application No. PCT/US2018/067687 dated Mar. 29, 2019.

PCT International Preliminary Report on Patentability of International Application No. PCT/US2018/067687 dated Mar. 31, 2020.

* cited by examiner

HI-FIDELITY BIOAEROSOL CONDENSATION CAPTURE DIRECTLY INTO GENOMIC PRESERVATIVES

CROSS-REFERENCE TO RELATED APPLICATIONS

The present application claims the benefit of U.S. Provisional Patent Application No. 62/611,907, filed on Dec. 29, 2017, which is incorporated herein by reference.

STATEMENT OF GOVERNMENTAL SUPPORT

This invention was made with government support under grant number IIP-1721940 awarded by the National Science Foundation. The government has certain rights in the invention.

FIELD OF THE INVENTION

This invention relates generally to characterizing bioaerosols and, more particularly, to a system for recovering, quantifying, identifying, and assessing the metabolic activities of bioaerosols based on their major biopolymer profiles (lipids, carbohydrate and protein) and more specific their genetic materials (DNA/RNA), such as airborne viruses, bacteria, fungi and pollens.

BACKGROUND OF THE INVENTION

"Bioaerosols" are broadly defined as any airborne compound of biological origin, they are defined here as any intact airborne cells, notably including airborne microbes of any kind, their airborne component parts, and/or dissociated airborne genetic materials (AKA: relic DNA). Bioaerosols typically occur in significantly lower concentrations than their microbial counterparts in aqueous and terrestrial media, making more difficult to characterize using genetic analysis methods. Bioaerosols are ubiquitous in the atmosphere; both indoors and out. Bioaerosols and can notably be found in the workplace, in residences, in medical facilities, in manufacturing operations, in animal processing facilities, in dairy facilities or other animal houses, in recycling or composting plants, in sanitary landfills, in sewage plants, etc. As bioaerosols of airborne microorganisms are a natural part of terrestrial and marine ecosystems, and are present in the atmosphere at large, but can cause disease, allergies, and respiratory problems in humans and mammals. Bioaerosols are increasingly feared for their potential use as biological warfare agents; including as terrorist weapons.

There are many aerosol sampling and detection systems; however, most of them are used for the analysis non-biological materials, and regardless of their design intents can not reliably preserve viability of bioaerosols or their genetic materials as they exist suspended in air. Furthermore, conventional aerosol sampling is not capable of separating and distinguishing airborne biological agents from their inorganic counterparts collocated in the same sample volume. The commonly used sampling method for recovering, then quantifying and subsequently identifying airborne microbes include the following: direct impaction of air onto agar, or other solid phase surface, using samplers such as the Andersen impactor [1] and Burkard impactor; direct filtration, such as surface air systems (SAS); and centrifugal collection, such as the Reuter centrifugal system (RCS). Bioaerosols can also be collected by impingement into liquid media such as the SKC biosampler, or other swirling liquid cyclone samplers, such as the SpinCon and its variants. While a number of (bio)aerosol samplers have been specifically designed to recover airborne microbial cells, it is clear that these systems share a salient limitation that upon collection, stress of the microbial cells, or otherwise modification their physiology such that their membranes, viability, internal biopolymer pools, notably including their genetic materials, are permanently and significantly altered from their airborne state.

Existing bioaerosol collection methods thus affect the quantitative and qualitative data that can be drawn from them, after processing, Therefore, there is a continued need for improved methods and devices for high efficiency and hi-fidelity bioaerosol capture.

SUMMARY OF THE INVENTION

This invention relates generally to bioaerosols and, more particularly, to a system for recovering and preserving the physiologic and biochemical integrity of microbial bioaerosols for subsequent detection and characterization.

In one embodiment, the invention contemplates a method of sampling while concomitantly stabilizing bioaerosol materials comprising; a) providing; i) a condensation growth tube; and ii) an aerosol stream comprising water vapor, and/or other reagent vapor and mixed or pure substance, bioaerosol materials; b) directing said aerosol stream into said tube under said conditions that said water vapor, or other reagent vapor, condenses on said bioaerosol particles so as to form microdroplets; and c) collecting all individual droplets into individual, sterile, RNA-free and DNA-free containers, containing a genomic, transcriptomic, protein and/or lipid preservative(s). In one embodiment, said condensation growth tube capture comprises a wet-walled tube that comprises a region of supersaturation in the aerosol stream. In one embodiment, said condensation growth tube comprises a sample inlet connected directly to a conditioner tube wall section. In one embodiment, the condensation growth tube comprises an initiator tube wall section. In one embodiment, the condensation growth tube comprises a moderator tube wall section. In one embodiment, the condensation growth tube comprises a tapered aperture. In one embodiment, said tapered aperture directs collected (bio) aerosol into a terminal collection well, or other container, containing a liquid (regardless of viscosity), a gel or solid phase, including but not limited to those used to preserve genetic materials, proteins or lipids. In one embodiment, said container comprises a tube used for subsequent biochemical or genetic analysis. In one embodiment, said container comprises a well, microwell, series of microwells, a tube, microcentrifuge tube, series of microcentrifuge tubes, titer well, microtiter well, series of microtiter wells, microtiter plates other container used for biochemical and/or genetic analysis such as an ELISA plate, tissue culture plate or virus plaque plate, with any number of wells. In one embodiment, the method further comprises nucleic acid (DNA and/or RNA) purification, quantitation and sequencing of said bioaerosol genetic materials. In one embodiment, the method further comprises amplification of nucleic acid from said bioaerosol materials and quantification of said nucleic acid materials (DNA and/or RNA): In one embodiment, the method further comprises (bio)chemical analysis of said bioaerosol materials, including proteins and lipid materials. In one embodiment, said tapered aperture directs collected (bio)aerosol onto a terminal solid phase collection site of impaction surface, solid membrane filter, solid woven fiber filter which is saturated with, sorbed to, or otherwise retains chemicals used to preserve genetic materials, proteins or lipids.

In one embodiment, the invention contemplates a bioaerosol detection system comprising: a) a condensation growth tube comprising a sample inlet connected directly to a moderator tube wall section followed by an tapered aperture to condense or otherwise bind a biocompatibie liquid, a physiologic preservative, a genomic preservative, and/or biological stain with one or more bioaerosols of a continuously flowing sample volume; b) at least one sterile RNA/DNA-free container, impaction surface or filter material positioned underneath said tapered aperture; and c) an amplifier to allow a size amplification of the one or more bioaerosols of the continuously flowing sample volume from said tube. In one embodiment, said tube further comprises an initiator tube wall section. In one embodiment, said tube further comprises a moderator tube wall section. In one embodiment, said conditioner tube wall section comprises a cold area of tube wall that is a few degrees above the freezing temperature of water or the freezing temperature of water, or a condensing reagent vapor introduced to and flowing through the initiator. In one embodiment, said initiator tube wall section comprises a warm area of tube wall that is approximately 35° C. (or at least 25° C. above the temperature of the conditioner region). In one embodiment, said moderator tube wall section comprises a cool area of tube wall that is approximately 12° C., but is adjusted from this point to optimize bioaerosol capture based on local environmental temperature, and/or the condensation point of water or any reagent vapor introduced to, and flowing through the initiator.

There are other means of condensing vapor onto bioaerosols to form microdroplets in-situ (Peter H. McMurry (2000) The History of Condensation Nucleus Counters, Aerosol Science & Technology, 33:4, 297-322 [2]; U.S. Pat. No. 3,738,751 [3], 3806248 [4], 4449816 [5], 4790650 [6], 4868398 [7], 4950073 [8], 5675405 [9], 5855652 [10], 6506345 [11], 6567157 [12], 6980284 [13], 7777867 [14], 7828273 [15], 8449657 [16], 8465791 [17], 8603247 [18]). These include, but are not limited to: a) laminar-flow sampling through wet-walled tubes or chambers comprised of at least two temperature regions with the first region warm followed by a cooled region, b) turbulent mixing of two or more vapor streams each held at different temperatures, and c) rapid adiabatic expansion of a vapor saturated chamber.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

As used herein, the term "bioaerosols" is used throughout to describe airborne particles that are biological in origin, such as airborne microbes. Bioaerosols can be formed from nearly any process that involves biological materials and generates enough energy to separate small particles from the larger substance, such as wind, water, air, or mechanical movement.

As used herein, the term "genomic preservative" is used throughout to describe any compound which is designed and serves to conserve, protect or otherwise maintain the biochemical structure of DNA and RNA, regardless of origin.

As used herein, the term reagent vapor is used throughout to describe any compound, other than water, which is introduced to the device which serves to change phase condense through the device on particles, grow particle size, and enable the capture of particles as described for water above, although different temperature profiles will be associated with the process (initiator, moderator, tapered aperture, etc.) with the condensation process as described with water.

As used herein, the terra "transcriptome preservative" is used throughout to describe protect or otherwise maintain the biochemical structure of RNA, in all its forms ribosomal, transfer or messenger regardless of origin As used herein, the term "microdroplets" is used throughout to describe to airborne condensates of liquid water or other reagent, either alone, or on the surface of other airborne particles, where the characteristic length of the conglomerate drop is less than 1 millimeter. This includes, but is not limited to, water vapor that is adsorbed, and/or absorbed to airborne particles that is not free water associated with the particle surface.

As used herein, the term "amplify" is used throughout to describe the biochemical method for replicating the sequence of any biopolymer, including DNA, RNA or Protein, or its precursors, this includes but is not limited to polymerase chain reaction (PCR)

As used herein, the term "RNA/DNA-free container" is used throughout to describe any container, vessel, well, tube or conduit that is rendered free of polymerized genetic materials that are capable of being amplified by polymerase chain reaction (PCR), or otherwise detected as oligonucleotides of DNA and/or RNA.

As used herein, the term "microwell" is used throughout to describe any container, vessel or tube which is less than 1 milliliter in volume for each 1 liter per minute of sample flow intended to hold a liquid or solid for chemical analysis

BRIEF DESCRIPTION OF THE DRAWINGS

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

This invention is described in preferred embodiments in the following description with reference to the Figures, in which like numbers represent the same or similar elements.

DETAILED DESCRIPTION OF THE INVENTION

The described features, structures, or characteristics of the invention may be combined in any suitable manner in one or more embodiments. In the following description, numerous specific details are recited to provide a thorough understanding the preferred of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

A known method of detecting and identifying bioaerosols is disclosed in U.S. Pat. No. 6,806,464 [23] (herein incorporated by reference). An aerosol time-of-flight mass spectrometer using fluorescence techniques is used to ionize selected bioaerosol particles. Laser radiation using a wavelength which is specific to substances affects fluorescence. A fluorescence detector is used to select the bioaerosol particles, and a second laser is used to emit light of a wavelength that effects the ionization of the bioaerosol particles selected by the fluorescence detector. Such a method of detecting and identifying a bioaerosol is rather complex, relying on relatively expensive and complex equipment. Furthermore, this is a destructive method which cannot provide information regarding microbial viability and has not been demonstrated to be able to accurately provide genetically-based taxonomic information regarding genera or species, in practical applications.

Other methods for bioaerosol sampling rely on impaction or impingement. This is accomplished using inertial forces either by impaction on plates, such as that used in an Anderson Impactor (Copely Scientific), loaded with agar or by impingement into a liquid, such as that used in an All Glass Impinger (ACE Glass Incorporated) or a BioSampler (SKC Inc.) (U.S. Pat. No. 5,902,385 [24]) (herein incorporated by reference). Because inertia is a function of particle size, particle size plays a critical role in determining the ability to sample and quantify bioaerosols; in general, the larger the size, the higher the collection efficiency.

An impactor is a device with nozzles that direct air flow carrying aerosol toward impaction plates or filters which serve as a collection media. The inertia of the aerosol particles drives its impaction, and therefore its collection efficiency decreases as particle size decreases. The collection efficiency can be increased by applying pressure or by applying a higher velocity. Filtration is a method of separating particles from the carrier gas by collecting the particles on filter media as the gas passes through open pores or structures of the filter material. Particles make contact with the filter media; and other particles previously deposited on the media, by impaction, interception or diffusion, with each removal mechanism being strongly dependent on particle size. While impaction and filtration can be highly efficient at collecting particles, these approaches stress airborne microbes through high velocity impact and desiccates cells as they are collected; the physiological effects of impact, shearing and desiccation associated with these types of aerosol recovery devices introduce tremendous artifacts regarding cellular damage and thus cannot be used for viability or quantitative genetic analyses with any reasonable degree of certainty. Therefore impaction and filtration cannot be used for observing viable bioaerosols or quantitation using genetic methods.

An impinger is a container with nozzles and an aqueous collection medium. Air flow exiting the inlet nozzle(s) form bubbles in the liquid. Aerosol particles in the bubbles can leave the bubbles due to its inertia, and therefore the collection efficiency decreases as its particle size decreases. Available impingers such as All Glass impingers have less than 70% efficiency for particles less than 0.5 µm. The BioSampler, which is an improved version using swirling jets, still has only 80% efficiency for 0.3 µm. As described, either a viable impactor or an impinger has low efficiency for bioaerosols below 0.3 µm. According to Hogan et al. ("Sampling Methodologies and Dosage Assessment Techniques for Submicrometer and Ultrafine Virus Aerosol Particles", Applied Microbiology, 99, p. 1422-1434, 2005 [25]), the efficiency of BioSamplers and All Glass Impingers for collecting MS2 bacteriophage is less than 10%. Further, liquid impingers have variable recovery efficiency where hydrophobic airborne microbes are concerned, including for example fungal spores, the bacteria belonging to the family of Actinomycetes, notably including Mycobacteria species. While bioaerosols impinged in liquid experience less impact stress than their counterparts collected in impactors, these devices also impart significant physiological stress. This stress is realized by bioaerosols approaching sonic speeds and large pressure drops through the collection nozzles, and once in the impinger reservoir, stress is realized by impinger reflux, rapid evaporation and cold temperature (<10 C), all of which introduce uncertainties in subsequent genetic and biochemical analysis of the impinger contents.

Thus, there is a need to overcome these and other problems of the prior art and to provide a bioaerosol recovery system that has high capture efficiency, minimizes physiological stress and recovers airborne microbes directly into preservative(s), or onto surfaces saturated with sorbed to, or otherwise associating with preservatives, including but not limited to membranes and filters, that maintain biopolymers with hi-fidelity. Air filters, impactors, and liquid impingers are among the most common alternatives for sampling airborne microbes (bioaerosols). While these low-tech collection methods are cheap, easy and popular, they are fraught with problems for modern aerobiology analysis. Filters impart intense mechanical and desiccation stresses on airborne microbes upon collection. Further, they must elute and dilute samples for further processing that drastically affects sensitivity (PCR and or sequencing); they require tedious, time-intensive, multi-step manual processing; have low extraction efficiencies; and are prone to contamination. Because of low biomass yields, filter-based collection makes it impossible to recover time-resolved samples during periods that are relevant to observing microbial activity in-situ.

One embodiment of the current invention device condenses humidity in a device that concentrates ambient bioaerosols directly into thin films and liquids that preserves genetic materials on contact. Although it is not necessary to understand the mechanism of an invention, it is believed that this condensation process stabilizes bioaerosol genetic materials as they are collected from air, in a small-volume convenient for subsequent DNA/RNA amplification and/or sequencing and (bio)chemical analyses.

Figure 1:
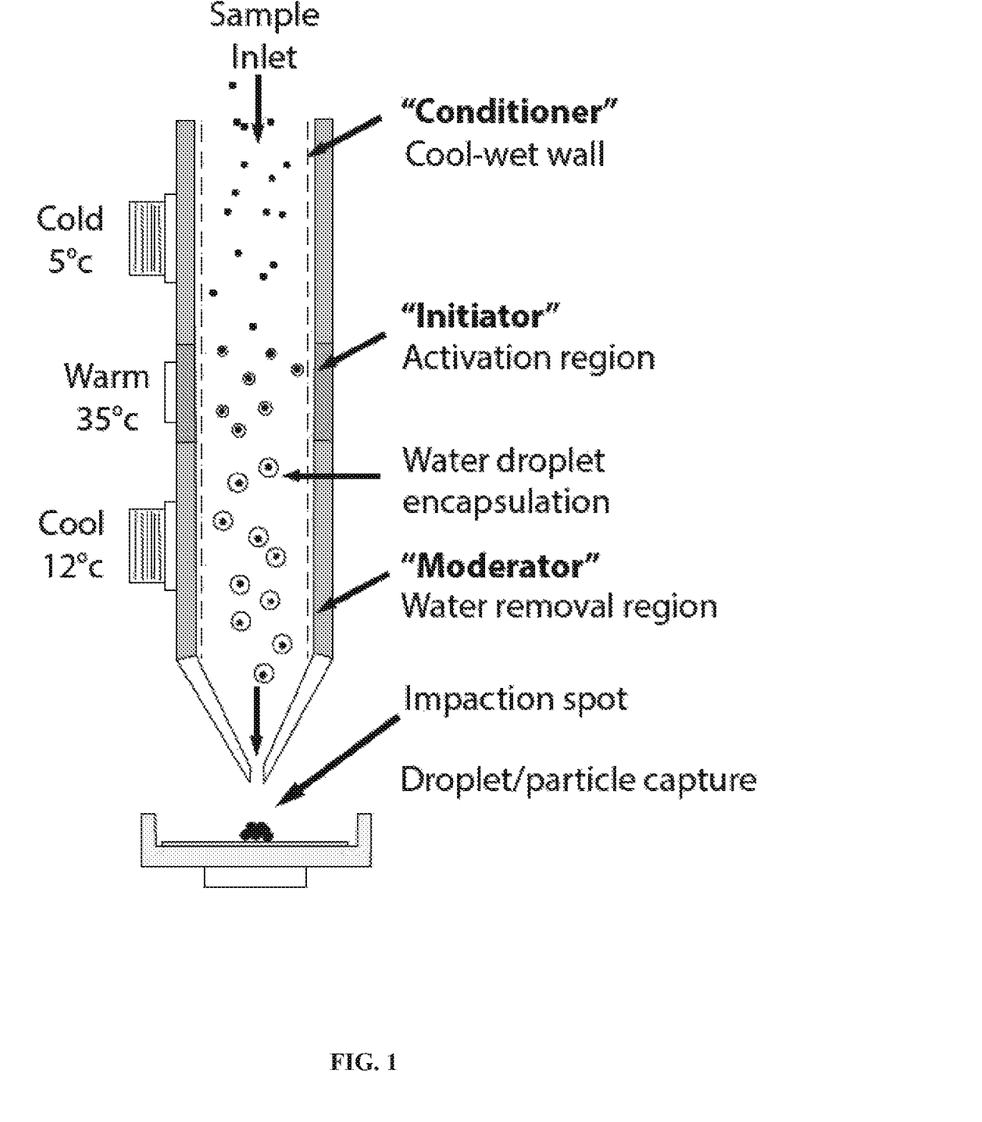
FIG. 1 shows one embodiment of the condensation capture process using a condensation growth tube capture (CGTC) apparatus (U.S. Pat. No. 6,712,881 [19], U.S. Pat. No. 7,736,421 [20], U.S. Pat. No. 8,801,838 [21], and U.S. Pat. No. 9,610,531 [22]).

One embodiment of the current invention is shown in a schematic describing condensation growth tube capture (CGTC) apparatus in FIG. 1. Although it is not necessary to understand the mechanism of an invention, it is believed that this sampling method moderates temperature under laminar-flow, in a wet-walled tube to create a region of supersaturation in the aerosol stream. The supersaturated water vapor absorbs, adsorbs and/or otherwise condenses on bioaerosol particles enlarging them to form microdroplets, that can be analogous to a "fog". The microdroplets may remain independent or agglomerate; but regardless, each droplet is then directly collected by gentle, low-velocity impingement into wells, microwells or any analytical tube or containment with a genomic (DNA and RNA), transcriptomic (RNA of any kind), protein and/r lipid preservative. Although it is not necessary to understand the mechanism of an invention, it is believed that this sampler efficiently collects >95% airborne microbes in the size range of viruses, bacteria and fungal spores and avoids the stress and analytical recovery problems introduced by filters and impactors.

Genetic material can be aseptically recovered from CGCT wells in liquid preservatives used to prepare samples for DNA and RNA quantitation and sequencing on popular high throughput platforms. This CGCT device may be portable, and has use in the laboratory and in the field. In controlled bioaerosol chamber studies, total gene copy numbers as determined by qPCR with universal bacterial (16s rDNA) and have been quantitatively compared to direct microscopic counts with reproducible quantitative agreement.

Figure 2:
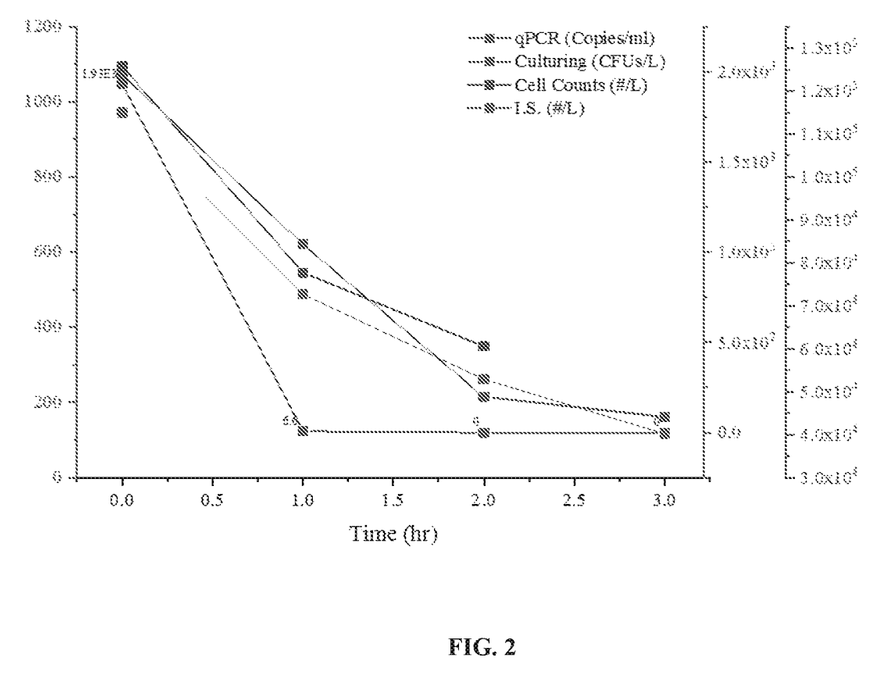
FIG. 2 shows the recovery of whole cell airborne bacteria from CGTC into microwells filled with preservative used for microbiological analysis of DNA by quantitative polymerase chain reaction (qPCR ▩, pink), in parallel with direct microscopy (▩, blue), direct fluorescent particle counts (cytometry ▩, red); and standard culturing (▩, green).

FIG. 2 shows the recovery of whole cell airborne bacteria from CGTC into microwells filled with liquid preservative used for microbiological analysis of DNA by quantitative polymerase chain reaction (qPCR ※ ), in parallel with direct microscopy (※ ), direct fluorescent particle counts (cytometry ※ ); and standard culturing (※ ).

Figure 3:
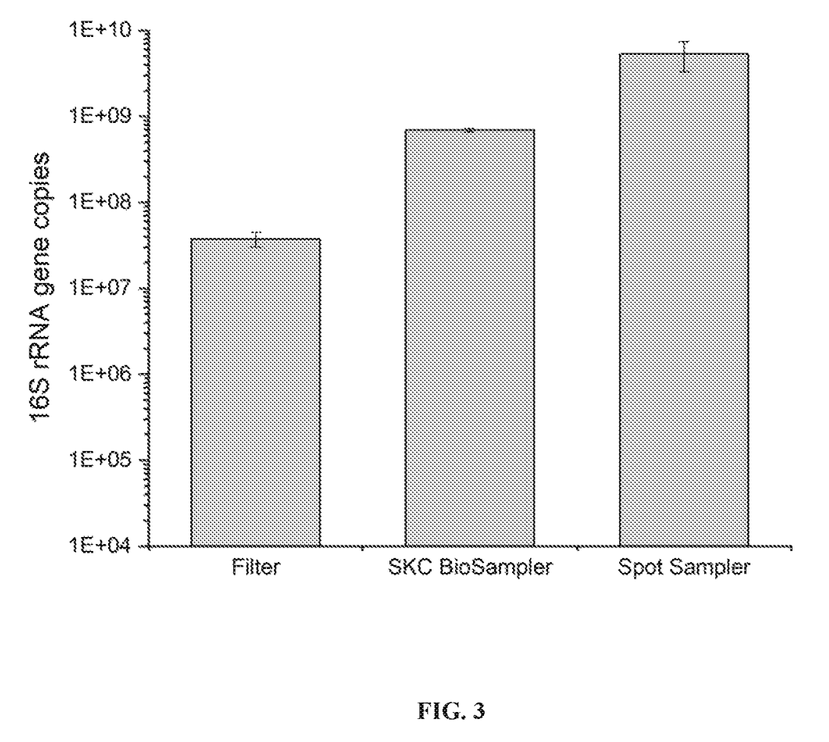
FIG. 3 shows the recovery of whole cell airborne bacteria from CGTC into microwells filled with preservative used for microbiological analysis of DNA by quantitative polymerase chain reaction (qPCR ▩) as compared to concurrent sampling of the same bioaerosol with conventional filtration and the most common liquid impinger (SKC Biosampler), used for the bioaerosol capture.

FIG. 3 compares the recovery of conventional filters, liquid impingers and CGTC collecting directly in liquid genomic preservative. In this comparison, the filter, liquid impinger and CGTC concurrently collected bioaerosol from the same calibrated source. As judged by quantitative PCR using 16s rDNA as the target amplicon, CGTC into liquid preservative has at least an order of magnitude better recovery performance when compared, side-by-side, with conventional filtration and liquid impingement.

Since quantitative PCR is successful with between 100 and 2000 airborne cells captured in 10 minutes), the relative abundance of different DNA sequences using CTGC in this preservative capture scenario, can thus likely be reduced into microbial community structures from environmental samples using accepted statistical bioinformatics approaches developed for this purpose. Although it is not necessary to understand the mechanism of an invention, it is believed that being able to characterize airborne microbes and assess their activity, as they exist in-situ may lead to a high fidelity preservation of bioaerosol transcriptomes using CTGC in this scenario. It is further believed that the physical and temporal collection of artifacts that bias aerosol DNA sequencing, and previously prohibited or otherwise impacted RNA recovery, specifically mRNA recovery, are mitigated by condensation collection in this CGTC platform where genomic and/or transcripomic preservatives are used for terminal particle capture. Although it is not necessary to understand the mechanism of an invention, it is believed that in this configuration, CGTC facilitates non-damaging genome and/or transcriptome recovery from bioaerosols in a way that was not previously possible.

Thus, specific compositions and methods of hi-fidelity bioaerosol condensation capture directly into genomic preservatives have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

REFERENCES

1. Xu, Z. et al. (2013) "Enhancing Bioaerosol Sampling by Andersen Impactors Using Mineral-Oil-Spread Agar Plate," *PLoS. ONE* 8(2), e56896.
2. McMurry, P. H. (2000) "The History of Condensation Nucleus Counters," *Aerosol Sci. Technol.* 33(4) 297-322.
3. Rich, T. "Portable Condensation Nuclei Meter," U.S. Pat. No. 3,738,751, application Ser. No. 05/056,834, filed Jul. 21, 1970, (issued Jun. 12, 1973).
4. Sinclair, D. "Continuous Flow Condensation Nuclei Counter," U.S. Pat. No. 3,806,248, application Ser. No. 05/334,497, filed Feb. 21, 1973, (issued Jun. 12, 1973).
5. Kohsaka, Y et al. "Method for Measuring the Number of Hyperfine Particles and a Measuring System Therefor," U.S. Pat. No. 4,449,816, application Ser. No. 06/262,550, filed May 11, 1981. (issued May 22, 1984).
6. C. Kohsaka, Y et al. "Condensation Nucleus Counter," U.S. Pat. No. 4,790,650, application Ser. No. 07/040,540, filed Apr. 17, 1987. (issued Dec. 13, 1988).
7. Mulcey, P. et al, "Device for the Real Time Measurement of the Content of an Aerosol in a Gas," U.S. Pat. No. 4,868,398, application Ser. No. 07/164,056, filed Mar. 3, 1988. (issued Sep. 19, 1989).
8. Sommer, H. T. "Submicron Particle Counting Enlarging the Particles in a Condensation Based Growth Process," U.S. Pat. No. 4,950,073, application Ser. No. 07/308,556, filed Feb. 10, 1989. (issued Aug. 21, 1990).
9. Schildmeyer, F. C. and Shahan, B. J. "Condensation Nucleus Counter Employing Supersaturation by Thermal Differentiation," U.S. Pat. No. 5,675,405, application Ser. No. 08/695,658, filed Aug. 12, 1996, (issued Oct. 7, 1997),
10. Talley, R. "Aerosol Collector and Concentrator," U.S. Pat. No. 5,855,652, application Ser. No. 08/792,528, filed Jan. 5, 1999. (issued Jan. 5, 1999).
11. Talley, R. "Apparatus for Rapid. Measurement of Aerosol Bulk Chemical Composition," U.S. Pat. No. 6,506,345, application Ser. No. 09/679,704, filed Oct. 5, 2000. (issued Jan. 14, 2003).
12. Flagan, R. C. and Wang, J. "Fast Mixing Condensation Nucleus Counter," U.S. Pat. No. 6,567,157, application Ser. No. 09/688,411, filed Oct. 12, 2000. (issued May 20, 2003).
13. Ahn, K.-h. et al, "Condensation Panicle Counter," U.S. Pat. No. 6,980,284, application Ser. No. 10/381,251, filed Dec. 27, 2005. (issued May 20, 2003),
14. Hopke, P. K. and Ambs, J. L. "Devices, Methods, and Systems for Detecting Particles in Aerosol Gas Streams," U.S. Pat. No. 7,777,867, application Ser. No. 11/615,672, filed Aug. 17, 2010. (issued May 20, 2003).
15. Mölter, L. and Munzinger, F. "Method and Apparatus for Humidifying Gas and for Condensing Steam on Condensation Nuclet," U.S. Pat. No. 7,828,273, application Ser. No. 12/410,798, filed Mar. 25, 2009. (issued Nov. 9, 2010).
16. Son, S, Y. et al. "Continuous Droplet Generator Devices and Methods," U.S. Pat. No. 8,449,657, application Ser. No. 12/689,520, filed Jan. 19, 2010. (issued May 28, 2013).
17. Liu, B. Y. H. et al. "Method for Counting Particles in a Gas," U.S. Pat. No. 8,465,791, application Ser. No. 12/872,697, filed Aug. 31, 2010. (issued Jun. 18, 2013).
18. Liu, B. Y. H. et al. "Apparatus for Counting Particles in a Gas," U.S. Pat. No. 8,603,247, application Ser. No. 13/887,554, filed May 6, 2013. (issued Dec. 10, 2013).
19. Hering, S. V. and Stolzenburg, M. R. "Continuous, Laminar Flow Water-Based Particle Condensation Device and Method," U.S. Pat. No. 6,712,881, application Ser. No. 10/354,419, filed Jan. 30, 2003, (issued Mar. 30, 2004),
20. Hering, S. and Lewis, G. "High Saturation Ratio Water Condensation Device and Method," U.S. Pat. No. 7,736,421, application Ser. No. 11/868,163, filed Oct. 5, 2007, (issued Jun. 15, 2010).
21. Hering, S. V et al. "Advanced Laminar Flow Water Condensation Technology for Ultrafine Particles," U.S. Pat. No. 8,801,838, application Ser. No. 13/218,393, filed Aug. 25, 2011. (issued Aug. 12, 2014).
22. Hering, S. V et al. "Wick Wetting for Water Condensation Systems," U.S. Pat. No. 9,610,531, application Ser. No. 14/043,455, filed Oct. 1, 2013. (issued Apr. 4, 2017),
23. Stowers, M. A. et al, "Method and Device for Detecting and Identifying Bio-Aerosol Particles in the Air," U.S. Pat. No. 6,806,464, application Ser. No. 10/450,638, filed Dec. 10, 2003. (issued Oct. 19, 2004).
24. Willeke, K. et al. "Swirling Aerosol Collector," U.S. Pat. No. 5,902,385, application Ser. No. 08/880,118, filed Jun. 23, 1997. (issued May 11, 1999).
25. Hogan, C. J. et al. (2005) "Sampling Methodologies and Dosage Assessment Techniques for Submicrometre and Ultrafine Virus Aerosol Particles," *J. Appl. Microbiol.* 99(6), 1422-1434.

We claim:

1. A method of sampling, recovering and stabilizing bioaerosol materials comprising;
   a) providing;
      i) a condensation growth tube; and
      ii) an aerosol stream comprising water vapor and bioaerosol materials;
   b) directing said aerosol stream into said tube-so that said vapor condenses on said bioaerosol particles so as to form microdroplets; and
   c) collecting individual and/or a conglomerate of said microdroplets into at least one individual, sterile DNA-free container containing a genomic, transcriptomic or proteomic preservative, wherein said microdroplets are simultaneously exposed to said preservative.

2. The method of claim 1, wherein the method further comprises step d) recovery of bioaerosol particles.

3. The method of claim 2, wherein said bioaerosol particles comprise microbial nucleic acids.

4. The method of claim 1, wherein preservation of said bioaerosol particles is quantitative.

5. The method of claim 1, wherein said condensation growth tube is RNA-free and DNA-free prior to use.

* * * * *

UNITED STATES PATENT AND TRADEMARK OFFICE
CERTIFICATE OF CORRECTION

| | | |
|---|---|---|
| PATENT NO. | : 11,662,280 B2 | Page 1 of 1 |
| APPLICATION NO. | : 16/958421 | |
| DATED | : May 30, 2023 | |
| INVENTOR(S) | : Mark Hernandez, Patricia B. Keady and Marina Nieto-Caballero | |

It is certified that error appears in the above-identified patent and that said Letters Patent is hereby corrected as shown below:

On the Title Page

Column 1, Item (72), Inventors: Line 4, add the below inventor:
Marina Nieto-Caballero, Fort Collins, CO (US)

Signed and Sealed this
Ninth Day of January, 2024

Katherine Kelly Vidal
*Director of the United States Patent and Trademark Office*